United States Patent [19]

Fisnerova et al.

[11] 4,136,194

[45] Jan. 23, 1979

[54] 2-PHENYL-2-CARBOXYETHYL 1-(P-CHLOROBENZOYL)-5-METHOXY-2-METHYL-3-INDOLYLACETATE AND PROCESS FOR PREPARATION THEREOF

[75] Inventors: Ludmila Fisnerova; Jaroslava Grimova; Zdenek Roubal; Oldrich Nemecek, all of Prague, Czechoslovakia

[73] Assignee: SPOFA, United Pharmaceutical Works, Prague, Czechoslovakia

[21] Appl. No.: 811,881

[22] Filed: Jun. 30, 1977

[30] Foreign Application Priority Data

Jun. 30, 1976 [CS] Czechoslovakia .................... 4324-76

[51] Int. Cl.$^2$ ................. C07D 209/30; A61K 31/405

[52] U.S. Cl. ........................... 424/274; 260/326.13 A
[58] Field of Search ................ 260/326.13 A; 424/274

[56] References Cited

U.S. PATENT DOCUMENTS 3,962,471  6/1976  Biere et al. .................. 260/326.13 A

*Primary Examiner*—Nicholas S. Rizzo
*Assistant Examiner*—D. B. Springer

[57] ABSTRACT

A technique is described for the preparation of a novel anti-inflammatory agent comprising 2-phenyl-2-carboxyethyl 1-(p-chlorobenzoyl)-5-methoxy-2-methyl-3-indolylacetate. The preparative technique involves reacting indomethacin with tropic acid.

2 Claims, No Drawings

2-PHENYL-2-CARBOXYETHYL 1-(P-CHLOROBENZOYL)-5-METHOXY-2-METHYL-3-INDOLYLACETATE AND PROCESS FOR PREPARATION THEREOF

This invention relates to a novel anti-inflammatory agent and to a method for the preparation thereof. More particularly, the present invention relates to 2-phenyl-2-carboxyethyl 1-(p-chlorobenzoyl)-5-methoxy-2-methyl-3-indoylacetate and to a method for its preparation.

Although the pharmaceutical industry has successfully developed a wide variety of anti-inflammatory agents during the past decade, workers in the art have continued to focus their attention upon the development of novel anti-inflammatory agents of low toxicity and high analgesic activity. In accordance with the present invention, this end is successfully attained by means of a novel indolylacetate which may be processed by conventional techniques for preparing medicinal dosages with known pharmaceutical excipients and auxiliaries and employed as the active ingredient of a safe and potent oral anti-inflammatory composition.

The compound of the present invention, 2-phenyl-2-carboxyethyl-1-(p-chlorobenzoyl)-5-methoxy-2-methyl-3-indolylacetate may conveniently be prepared by reacting 1-(p-chlorobenzoyl)-5-methoxy-2-methyl-3-indolylacetic acid (indomethacin) or a reactive derivative thereof with tropic (3-hydroxy-2-phenyl-propionic) acid. A suitable reactive derivative for this purpose is indomethacin imidazolide. Reaction of this compound with tropic acid in an inert organic solvent such as a halogenated aliphatic hydrocarbon having from 1-2 carbon atoms yields the desired compound. A particularly useful solvent for this purpose is dichloromethane.

A general discussion of alternative approaches for attaining the desired end follows. It will be understood that this discussion as well as the exemplary embodiments set forth hereinbelow are for purposes of exposition only and are not to be construed as limiting.

As noted above, indomethacin imidazolide is a suitable derivative for obtaining the inventive compound. This derivative may conveniently be obtained by reaction of carbonyldiimidazole in a conventional solvent of the type alluded to above with indomethacin and the resultant indomethacin imidazolide is reacted in situ, without an intermediary isolation or purification, with tropic acid to yield the ester of the invention.

An alternative technique for attaining the desired end involves reacting indomethacin with an equimolecular quantity of thionylchloride, desirably in a halogenated hydrocarbon solvent such as dichloromethane, at room temperature in the presence of imidazole which serves as a basic agent to bind hydrogen chloride formed during the process. The product of this reaction, 1-(p-chlorobenzoyl)-5-methoxy-2-methyl-3-indolylacetylchloride is then reacted, without isolation, with the equivalents of imidazole to yield indomethacin imidazole which is reacted with tropic acid, under the conditions set forth above, to yield the desired ester.

Still another alternative technique for preparing the compound of the invention involves reacting indomethacin with thionylchloride in a solvent such as toluene at room temperature in the presence of pyridine which serves as the basic binding agent for hydrogen chloride formed during the process. Reaction of the resultant 1-(p-chlorobenzoyl)-5-methoxy-2-methyl-3-indolylacetylchloride directly with tropic acid at elevated temperatures in a toluene solvent and in the presence of an equivalent quantity of pyridine.

Studies have revealed that the foregoing procedures are economical, simple and relatively safe. The reactions generally proceed at room temperature and the carboxyl group of the tropic acid need not be protected. Finally, purification of the desired ester may be effected by simple crystallization.

Several examples of the present invention are set forth below:

EXAMPLE 1

32.4 grams of carbonyldiimidazole (90%) was dissolved while stirring in a nitrogen ambient at room temperature in 400 ml of anhydrous dichloromethane. Next, 71.56 grams of indomethacin 1-(p-chlorobenzoyl)-5-methoxy-2-methyl-3-indolylacetic acid was added to the diimidazole, and ten minutes later 34 grams of tropic acid were added to the resultant mixture. Following, the mixture was stirred for five hours at room temperature. Then, the mixture was permitted to stand for 16 hours, was diluted with dichloromethane, washed successively with dilute hydrochloric acid and water to yield a neutral reaction product. The resultant dichloromethane solution was next dried over anhydrous magnesium sulfate, evaporated under reduced pressure to dryness and the solid residue crystallized from nitromethane. The yield of ester was 56 grams, melting point 130°–132° C. Subsequent concentration of mother liquors after crystallization yielded 10 grams of unreacted indomethacin. Analysis of the product yielded the following data:

$C_{28} H_{24} Cl N O_6$ - molecular weight 505.9

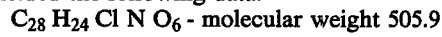

|  | % C | % H | % N | % Cl |
|---|---|---|---|---|
| Calculated | 66.47 | 4.78 | 2.77 | 7.00 |
| Found | 66.43 | 4.84 | 2.77 | 7.04 |

EXAMPLE 2

3.58 grams of a stirred suspension of indomethacin in a 36 ml. solution of anhydrous dichloromethane was reacted at room temperature under nitrogen iwth 0.68 grams of imidazole. Then, a solution of 1.19 grams of thionylchloride in 10 ml. of anhydrous dichloromethane was added dropwise to the mixture at a temperature from 10°–15° C. over a five minute interval. The mixture was then stirred for two additional hours at room temperature and then 1.36 grams of imidazole and 1.66 grams of tropic acid added. Stirring was continued for 5 hours and the mixture permitted to stand for 16 hours at room temperature. Following this, the procedure of Example 1 was utilized to recover the desired ester. One gram of the ester, melting point 128°–130° C. was obtained. Subsequent concentration of mother liquors after crystallization yielded 0.8 gram of indomethacin.

EXAMPLE 3

A stirred suspension of 14.28 grams of indomethacin in 640 ml of anhydrous toluene was mixed, at room temperature under nitrogen, with a solution of 3.16 grams of pyridine in 10 ml of toluene. The mixture was then cooled to 10° C. and a solution of 4.76 grams of thionylchloride in 15 ml of toluene was added dropwise thereto over a 5-minute interval at 10° C. Stirring was continued for 3 hours at room temperature and a mixture comprising 6.64 grams of tropic acid and 3.16 grams of anhydrous pyridine in 320 ml of anhydrous toluene added thereto. The reaction mixture was then stirred for 5 hours, permitted to stand for an additional 16 hours at room temperature and then warmed 4 hours to boiling. Upon cooling, the solution was washed with water, dried over anhydrous magnesium sulfate and evaporated under reduced pressure to dryness. Crystallization of the solid residue from nitromethane yields 3 grams of the ester, melting point 127°–129° C. Mother liquors after crystallization permitted the recovery of 2 grams of indomethacin.

The 2-phenyl-2-carboxyethyl 1-(p-chlorobenzoyl)-5-methoxy-2-methyl-3-indolylacetate prepared in accordance with the invention was evaluated by comparison with 1-(p-chlorobenzoyl-5-methoxy-2-methyl-3-indolylacetic acid), the widely-used anti-inflammatory substance indomethacin. The two compounds were compared upon oral administration of their aqueous suspensions, with the addition of gum arabic, into the stomachs of test animals using a flexible metallic probe.

Acute toxicity was determined by administering both compounds in a single dose to female mice weighing 16–20 grams (groups of ten) and female rats weighing 130–150 grams (groups of ten). The mortality rate was followed for 10 days after administration of the dosage. The median lethal doses, $LD_{50}$, are set forth in Table I below and were calculated by the method of J. Berkson, J. Am. Stat. Assoc. 50, 529, (1955).

TABLE I

| Acute Oral Toxicity in Mice and Rats | | |
|---|---|---|
| Compound | $LD_{50}$ Mice | mg/kg Rats |
| Indolylacetate of the invention | 190/170; 213/ | 140/125; 157/ |
| Indomethacin | 18/9; 26/ | 25/15; 35/ |

Anti-inflammatory activity was evaluated on kaolin oedema, carrageenin oedema and Freund adjuvant disease as standard model inflammatory syndromes in a group of six male rats.

The kaolin oedema of an extremity (J. Hillebrecht, Arzneim.-Forsch. 9, 625 (1969)) was produced in male rats weighing 130–150 grams by subplanatary injection of a 10% aqueous suspension of kaolin (0.1 ml). The indolylacetate of the invention and indomethacin were administered one hour before the injection of the suspension. The oedema size was measured 30 minutes, 3, 4.5 and 6 hours after the injection. The activity is conveniently expressed in percent of rate of inhibition in comparison with the untreated control group, the results being summarized in Table II below.

The carrageenin oedema (Ch. Winter, Proc. Soc. Exp. Biol. Med. 111, 544 (1962)) was produced in male rats weighing 130–150 grams by subplanatary injection of a 0.5% carrageenin solution (0.1 ml). The dosage schedule and assay procedure as well as the results were identical with those described above for the kaolin oedema inhibition test.

The adjuvant disease (J. Grimova, Physiol. Bohemoslovaca 20, 6 (1971)) was produced in male rats weighing approximately 100 grams by intradermal injection of 0.1 ml. of the Freund adjuvant into the caudal radix. The two compounds being tested were applied either in a single dosage simultaneously with the adjuvant injection (preventive dosage) or, in animals evidencing a maximum development of the disease, repeatedly over 21 days starting the 18th day after the injection (therapeutic dosage). The evaluation was made by estimating the animal motility, size of the posterior extremity oedema and X-ray pattern change in the extremity ossature. The results of these three series of tests are shown in Table II.

TABLE II

| Anti-Inflammatory Activity in Rats | | |
|---|---|---|
| Test Dosage | Compound of Invention | Indomethacin |
| Kaolin oedema inhibition, % 1 mg/kg p.o. | 16+ (4: 28) | 19+ (8: 31) |
| Carrageenin oedema inhibition, % 1.5 mg/kg p.o. | 15+ (6: 26) | 14+ (3: 28) |
| Adjuvant disease 3.5 and 3.0 mg/kg, respectively | | |
| Prevention: effect on oedema | +++ | ++ |
| effect on motility | + | ++ |
| X-ray changes | +++ | +++ |
| Therapy: effect on oedema | +++ | ++ |
| effect on motility | +++ | +++ |
| X-ray changes | ++ | ++ |

Analgesic activity was evaluated by the intraperitoneal irritation test with 3% acetic acid (L. B. Wilkin et al., J. Pharm. 133, 400 (1961)) in female mice weighing 16–20 grams (groups of 12 animals). The median effective doses $ED_{50}$ are set forth in Table III below.

TABLE III

| Analgesic Activity in Mice | | |
|---|---|---|
| | $ED_{50}$ | mg/kg |
| Compound of Invention | 24.5 | (23.6: 25.5) |
| Indomethacin | 14.5 | (9.7: 21.8) |

Gastrotoxicity (adversary effect on gastric mucosa, A. Robert, J. E. Nezamis, Proc. Soc. Exp. Biol. Med. 99, 443 (1958)) was monitored by oral administration of the compounds being compared by testing starving female rats of 250–300 grams body weight (group of six animals). The evaluation was made by estimating the frequency of gastric erosions and ulcers. The relative gastrotoxicity of the two compounds is expressed by the respective standard criteria, ulceration index, as indicated in Table IV below.

TABLE IV

| Gastrotoxicity in Rats | |
|---|---|
| Dosage | Ulceration Index |
| 30 mg/kg of inventive compound | 0 |
| 8 mg/kg of indomethacin | 300 |

What is claimed is:

1. 2-Phenyl-2-carboxyethyl 1-(p-chlorobenzoyl)-5-methoxy-2-methyl-3-indolylacetate.

2. Anti-inflammatory composition for the treatment of mammals in need thereof, consisting essentially of 2-phenyl-2-carboxyethyl 1-(p-chlorobenzoyl)-5-methoxy-2-methyl-3-indolylacetate as the active ingredient in combination with a pharmaceutical excipient and auxiliary.

* * * * *